US007197467B2

(12) United States Patent
Labadie

(10) Patent No.: US 7,197,467 B2
(45) Date of Patent: Mar. 27, 2007

(54) METHOD OF PROVIDING VISITATION SERVICES BETWEEN REMOTELY LOCATED PARTIES

(76) Inventor: Iris Labadie, P.O. Box 3343, Vista, CA (US) 92085

( * ) Notice: Subject to any disclaimer, the term of this patent is extended or adjusted under 35 U.S.C. 154(b) by 1264 days.

(21) Appl. No.: 09/947,282

(22) Filed: Sep. 5, 2001

(65) Prior Publication Data

US 2003/0046108 A1    Mar. 6, 2003

(51) Int. Cl.
*G06Q 99/00* (2006.01)

(52) U.S. Cl. .............................. 705/2; 705/3; 379/106.2

(58) Field of Classification Search ................ 600/300, 600/301; 379/106.02; 705/2, 3, 1
See application file for complete search history.

(56) References Cited

U.S. PATENT DOCUMENTS

| | | | |
|---|---|---|---|
| 5,732,231 A | | 3/1998 | Evans, III |
| 5,810,747 A | * | 9/1998 | Brudny et al. .............. 600/595 |
| 5,990,885 A | | 11/1999 | Gopinath et al. |
| 6,168,563 B1 | * | 1/2001 | Brown ........................ 600/301 |
| 6,205,716 B1 | | 3/2001 | Peltz |
| 6,249,809 B1 | * | 6/2001 | Bro ............................. 709/217 |
| 6,870,913 B2 | * | 3/2005 | Narasimhan et al. .. 379/106.02 |
| 2001/0051881 A1 | * | 12/2001 | Filler ............................. 705/3 |
| 2002/0152097 A1 | * | 10/2002 | Javors ............................ 705/2 |

FOREIGN PATENT DOCUMENTS

JP        02000305454 A    * 11/2000

OTHER PUBLICATIONS

Micorsoft, Computer Dictionary, 2002, Microsoft Press, Fifth Edition, p. 470, 474.*
Margo Harakas, Kid Cam Working Parents Can Log On and Watch Little Johnny at Day Care as More Centers Install Web Cams, Feb. 25, 2001, South Florida Sun—Sentinel, p. 1E.*
APE on the Web, The nursing home industry's critique of cameras: APE responds, Dec. 5, 1999, http://www.apeape.org/cams2.html.
APE on the Web, Virtual Visitation: Can the "granny cam" improve the quality of nursing home care?, Dec. 5, 1999, http://www.apeape.org/cams1.html.
Jim Murphy, Are Camera's "Orwellian"! We don't think so . . . , Dec. 5, 1999, http://www.apeape.org/orwell.html.

* cited by examiner

*Primary Examiner*—John Weiss
*Assistant Examiner*—Phyllis Daniels-Mendez
(74) *Attorney, Agent, or Firm*—Charles F. Reidelbach, Jr.

(57) ABSTRACT

With the development of a business that will supply a bonded visitation specialist to visit a patient or confined individual and supply personal caring contact that can make a person feel the much needed connection with family and friends, life can be made more enjoyable and healthy. In addition, with the advent of Internet technology and the latest video and audio recording and conferencing capabilities, these visitations can be made more personal, even if the caring family member is a great distance away. The professional visitation provider is a formal, dependable, unbiased, intermediary service that has been created to give family, friends and confined individual the sense of comfort that communication with a familiar person provides.

17 Claims, 1 Drawing Sheet

METHOD OF PROVIDING VISITATION SERVICES BETWEEN REMOTELY LOCATED PARTIES

FIELD OF THE INVENTION

Figure 1:
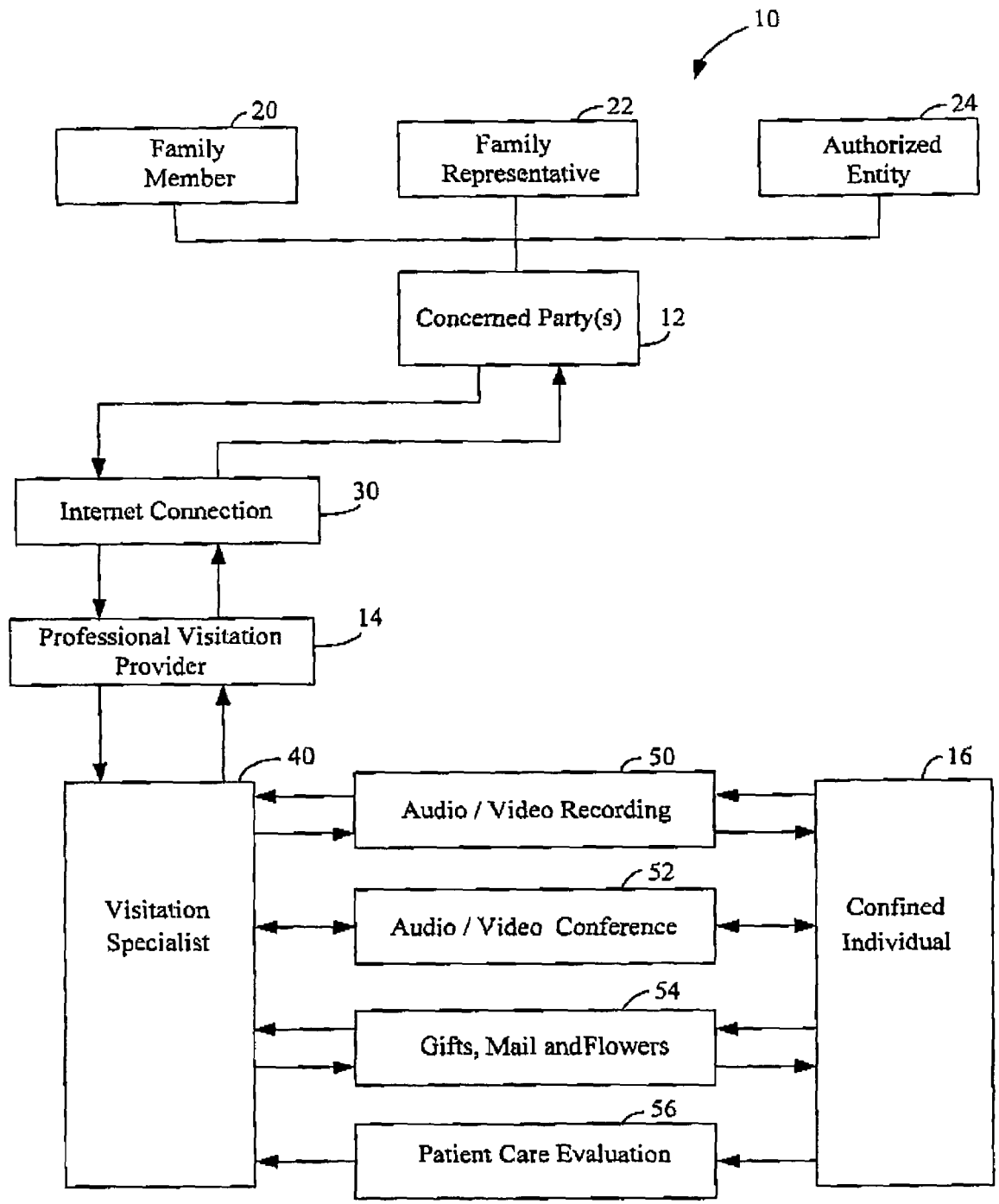

This invention generally relates to visitation services. More specifically, the present invention pertains to a method of contacting and hiring a professional visitation provider. The present invention is most useful, though not exclusively, for creating a business relationship where a concerned party(s) can hire a professional visitation provider to make predetermined visitations to monitor and facilitate in the communication with a patient or confined individual by utilizing communications technology, such as an audio recording, video and digital camera, and laptop computer, accessible though an Internet connection.

BACKGROUND OF THE INVENTION

While working within the health care industry for several years, the inventor has become aware that the care of patients or confined individuals, even in the best facilities, is considerably better when the confined individuals are closely monitored by family members or other concerned individuals. These confined individuals tend to live longer and have a much better outlook on life. The fact that family members can easily be scattered throughout the world, where they cannot maintain close ties with loved-ones that are confined to care facilities, is a major problem. In these typical circumstances, individuals may go for long periods, and sometimes indefinitely, with no attention from anyone except those in the care facility. In many other instances, there are no living family members to monitor the care of the confined individual.

The inventor is also aware that, at present, there are no organizations or businesses that will make regularly scheduled non-medical visits to confined individuals and communicate with their family members. With the advent of the computers, video conferencing, camera technology, cellular telephones and the World Wide Web, instant communication and verification of time and date has been made so easy, it leaves only the need for someone to establish a reliable business that can accomplish these tasks with a guarantee of integrity and personal service.

A recent report posted by APE ON THE WEB, entitled *Virtual Visitation: Can the "granny cam" improve the quality of nursing home care*,? dated Dec. 5, 1999, stated that of all means of preventing nursing home abuse and neglect, perhaps none are as effective as family involvement with the care of their loved-ones. Frequent visitation and observation not only send a clear message to the facility that the quality of care they are providing is being noticed, but is also the best way to detect problems of abuse and neglect at the early stages before they become severe or life threatening. Visitation is a fundamental right of all nursing home residents, but logistically it can be difficult for family members or concerned friends to visit as often as they like to assure that their loved-ones are receiving the care they deserve. It is a necessity and a responsibility to assure that a nursing home resident receives quality care, and abuse and neglect are quickly recognized and dealt with. Technology has provided a simple and efficient solution to the logistical barriers of day-to-day oversight of nursing home care, referring to a small, unobtrusive camera mounted so as to observe the patient at all times and transmit the images over the Internet to the family members. APE ON THE WEB is excited about the concept of "virtual visitation" and will provide an exhaustive examination of the technical, medical and ethical implications of the use of the "granny cam." It is clear to see the implications of using this device and how families of the patients may think of this as a great idea, while the care facilities would look at it as "big brother always watching" and are very much against the use of the device.

U.S. Pat. No. 5,990,885 issued to Gopinath, Bhaskarpillai et al. on Nov. 23, 1999, for an invention entitled, "Personalized Services, Including a Personal Presence, For Customers Based Upon Collected Personal Preferences," and describes an arrangement to provide personalized services to customers, such as hotel guests or hospital patients, where the personalized services are based upon a personal preference profile collection for each individual. The services are displayed to the guest or patient via an in-room monitor. Moreover, the personal preferences are modified during the guest's or patient's present stay, and saved after the stay for later visits. In addition, a personal presence of the host personnel, such as persons at a front desk or an admission desk, may be integrated into the display on the in-room monitor. This patent relates to the personal convenience and comfort of the individual, but not to communication of a confined individual with family members through an intermediary utilizing a secure communications network.

U.S. Pat. No. 6,168,563 issued to Stephen J. Brown et al. on Jan. 2, 2001, for an invention entitled, "Remote Health Monitoring and Maintenance System," and discloses a system and method that enables a health care provider to remotely monitor and manage a health condition of a patient. The system includes a health care provider apparatus operated by a health care provider and a remotely programmable patient apparatus that is operated by a patient. The health care provider develops a script program using the health care provider apparatus and then sends the script program to a remotely programmable patient apparatus through a communications network such as the World Wide Web. The script program is a computer-executable patient protocol that provides information to the patient about the patient's health condition and interactively monitors the patient health conditions by asking the patient questions and receiving answers to those questions. The answers to these health related questions are then forwarded as patient data from the remotely programmable patient apparatus to the health care provider apparatus through the communications network. The patient data may also include information supplied by a physiological monitoring device, such as a blood glucose monitor that is connected to the remotely programmable patient apparatus. When the patient data arrives at the health care provider apparatus, the patient data is processed for further management of the patient's health condition by the health care provider, such as forwarding another script program to the remotely programmable patient apparatus. This patent deals with the sensitive medical information and care of an individual within a facility, but again, not communication with family members through an intermediary on non-medical information.

U.S. Pat. No. 5,732,231 issued to Harry Evans, III, et al. on Mar. 24, 1998, for an invention entitled, "Funeral Home Display Monitor Apparatus," and describes an apparatus in a funeral establishment for displaying information about a deceased person whose visitation is or was in the funeral establishment. This invention does not in any way describe anything regarding the visitation of live individuals in care facilities.

U.S. Pat. No. 6,205,716 issued to Diane P. Peltz et al. on Mar. 27, 2001, for an invention entitled, "Modular Video Conferencing Enclosure," and discloses a secure, modular movable interactive two-way tele-collaborative video conferencing and imaging enclosure for conducting business or privileged medical, legal, or other confidential matters in private, being particularly equipped for remote monitoring of physiological attributes of one or more users by medical specialists and remote interaction between users and medical specialists. This patent also describes a device for conducting two-way interactive video conferencing from inside an enclosed structure, but does not suggest the use of an intermediary on non-medical information.

In accordance with the specified needs, Applicant submits a method for the establishment of a business that is devoted to those individuals confined in care facilities, or the like, and the communication to and from those who are concerned about them.

SUMMARY OF THE INVENTION

The present invention describes a method where family members or other loved-ones can contact and hire a professional visitation provider to make, but not limited to, predetermined visits to monitor and facilitate in the communication with a patient or individual confined to a premises. Visitation arrangements may be made by family members, a family or patient representative, or other entity with a professional visitation provider who employs a visitation specialist for a given number of visits on specified days to a confined individual. Preferably, the visitation will be made with the approval of the confined individual. The visitation specialist will make the visits equipped with the latest computer, video and audio recording, conferencing equipment, cellular telephone or other communication device. The visitation will occupy a designated period of time and the visitation specialist will deliver any gifts, mail or flowers from the family, and record the visit on an audio and/or video recorder. Any mail or gifts to be delivered to the family members will be picked up and transported to the professional visitation provider's offices where all messages and video will be transmitted to the recipient through a secure communications network, such as an Internet connection, and any gifts, mail or flowers will be sent by special delivery.

No medical treatment, care or implication thereof will be given by the visitation specialist, only general awareness of the environment, conditions and appearance compared to others in similar situations, will be provided. The visitation specialist will not be allowed to receive financial gifts from the family, confined individual or care facilities and will only be allowed to handle cash or checks in specially sealed envelopes with receipts recorded. All gifts and flowers will be billed through the professional visitation provider. The visitation specialist can be changed upon the request of either party involved.

The object of this invention is to complete a business transaction between a professional visitation provider and one or more concerned party(s) where non-medical visitation services are provided to a confined individual and the contents of the visitation are transmitted to the concerned party(s).

Another object of this invention is to supply the concerned party(s) and the confined individual with audio messages to each other.

An additional object of this invention is to supply the concerned party(s) and the confined individual with visual images of each other and the environments they are in.

Still another object of this invention is to create an up-to-date, real-time and simultaneous connection between the concerned party(s) and the confined individual in an environment located remotely.

Yet another object of this invention is to deliver gifts, mail and flowers between the concerned party(s) and the confined individual.

One more object of this invention is to establish a patient care evaluation that can be reviewed by the concerned party(s).

A further object of this invention is to establish a qualified intermediary to guarantee that all agreed upon visitations and transactions have been accomplished.

Another object of this invention is to establish a qualified intermediary that will employ enough visitation specialists to fulfill all the agreed upon visitations.

A final object of the invention is to create an unbiased third party, in the case of a dispute between the parties involved and the care facilities that will give both a visual representation of the conditions, and an accurate recorded comparison with other existing environments visited by the visitation specialist.

These, together with other objects and advantages that will become subsequently apparent, reside in the details of the method as more fully hereinafter described, claimed, and reference with an accompanying drawing where like numerals refer to like parts throughout.

BRIEF DESCRIPTION OF THE DRAWING FIGURE

FIG. 1 is a block diagram of the preferred embodiment showing the operational procedure for the concerned party (s) to hire a professional visitation provider to visit a confined individual.

DETAILED DESCRIPTION OF PREFERRED EMBODIMENTS

Referring now to FIG. 1, a block diagram of the preferred embodiment of Method of Providing Visitation Services Between Remotely Located Parties 10 and describes the operational procedure for concerned party(s) 12 to hire professional visitation provider 14 to visit and monitor confined individual 16. Concerned party(s) 12 may include, but is not limited to, family members 20, family representatives 22 and authorized entity 24.

The method begins when concerned party(s) 12 contacts professional visitation provider 14 through Internet connection 30, which could be by e-mail, web site chat-room or the web site address of professional visitation provider 14. Next, an agreement or contract between concerned party(s) 12 and professional visitation provider 14 is made through Internet connection 30. Concerned party(s) 12 can individually or jointly employ the services of, and establish a business relationship with, professional visitation provider 14. The unique payment method offered by professional visitation provider 14 allows each concerned party 12 to pay a pro-rated amount of the total service cost based upon the number of concerned parties 12 interested in the visitation service, and allows automatic debit from each concerned party's 12 credit card account. This payment transaction can be completed using Internet connection 30, such as the web site address of professional visitation provider 14. The pooling of resources in this manner allows for affordable frequent interaction of concerned party(s) 12 with confined individual 16. It is to be understood that confined individual 16 can independently establish a business relationship with professional visitation provider 14, if desired.

After an agreement between concerned party(s) 12 and professional visitation provider 14 is complete, professional visitation provider 14 assigns a visitation specialist 40 to make a predetermined number of visitations to confined individual 16. At each visitation, visitation specialist 40 can serve the functions of establishing audio/video recording 50, audio/video conference 52, delivering gifts, mail and flowers 54, and processing patient care evaluation 56. Visitation specialist 40 will most commonly utilize an interaction unit, such as a laptop computer, Personal Digital Assistant (PDA) and cellular phone, and input and output equipment to convey audio/video recordings 50 and audio/video conferences 52, to and from concerned party(s) 12 and confined individual 16. For example, the input equipment for audio/video recording 50 may include a video or digital camera, microphone or other similar device, and the output equipment may include a speaker, projection unit, monitor or other similar device. It should be noted that audio/video recording 50 is a one-way transmission of information. The input and output equipment for audio/video conference 52 are similar to audio/video recording 50, except audio/video conference 52 is a simultaneous transmission of information that can be two-way or more, depending on the number of concerned party(s) 12.

In addition to establishing audio/video recording 50 and audio/video conference 52, visitation specialist 54 will transport or arrange the transportation of gifts, mail or flowers 54 to and from concerned party(s) 12 and confined individual 16. It should be noted that gifts, mail or flowers 54 may be purchased from professional visitation provider's 14 website by concerned party(s) 12 and confined individual 16. At the visitation, the visitation specialist 40 will stay the required time period and create a patient care evaluation 56, which will be an evaluation of the conditions of confined individual 16 and the environment compared to other environments visited. After the visitation, the contents of the visitation will be stored on a server of professional visitation provider 14 for concerned party(s) 12 to access through Internet connection 30, such as the web site address of professional visitation provider 14. Concerned party(s) 12 and confined individual 16 will be given a unique security code that will allow them to access the contents on the server of professional visitation provider 14.

While the present invention has been described herein, various changes and substitutions are intended in the foregoing disclosure, and it will be appreciated that in some instance some features of the invention will be employed without a corresponding use of other features without departing from the scope of the invention as set forth.

I claim:

1. A method of providing personalized visitation services to a confined individual through the use of an independent third party professional visitation provider, comprising the steps of:
   establishing a business relationship between one or more concerned party(s) and the professional visitation provider;
   obtaining pre-approval for a visitation from the confined individual or a legal representative;
   assigning a visitation specialist to conduct a visitation[s] to the confined individual;
   providing an interaction unit for communication between the concerned party(s) and the confined individual;
   conducting the visitation between the concerned party(s) and the confined individual by the visitation specialist:
   creating a recording of the visitation between the visitation specialist and the confined individual;
   storing the recording of the visitation on a secured server for the concerned party(s) and the confined individual to access through an Internet connection; and
   providing a unique security code for the concerned party(s) and the confined individual to access the recording of the visitation on the secured server.

2. A method as recited in claim 1, wherein the interaction unit is a laptop computer, Personal Digital Assistant (PDA), cellular phone or other easily transportable information processing device.

3. A method as recited in claim 1, wherein the Internet connection is e-mail, chat-room, web site address, other connection on the World Wide Web or any protocol on the Internet that can transfer information.

4. A Method as recited in claim 1, wherein the method further comprises a patient care evaluation of the confined individual by the visitation specialist.

5. A method as recited in claim 4, wherein the patient care evaluation is stored on the secured server accessible by the concerned party(s) through the Internet connection.

6. A method as recited in claim 1, wherein the method further comprises arranging for the delivery of gift items between the concerned party(s) and the confined individual.

7. A method as recited in claim 6, wherein the concerned party(s) orders from professional visitation provider gifts, mail or flowers through the Internet connection to be delivered to confined individual by visitation specialist.

8. A method as recited in claim 6, wherein the confined individual orders from the professional visitation provider gifts, mail or flowers through the Internet connection to be delivered to the concerned party(s) by the visitation specialist.

9. A method as recited in claim 1, wherein the step of establishing a business relationship between the professional visitation provider and one or more concerned party(s) includes a payment from the concerned party(s) to the professional visitation provider in a pro-rated amount based upon the number of the concerned party(s).

10. A method as recited in claim 1, wherein the interaction unit has input and output means for communicating between the concerned party(s) and the confined individual.

11. A method as recited in claim 10, wherein the input means receives information and is a touch screen, keyboard, video camera; digital camera, cellular phone or microphone.

12. A method as recited in claim 10, wherein the output means is a speaker, monitor, projection unit or other visual display device.

13. A method as recited in claim 10, wherein the interaction unit is a one-way communication device that stores the information that is received from the concerned party(s) and the confined individual.

14. A method as recited in claim 10, wherein the interaction unit is a two-way or more communication device that simultaneously transfers, transmits and displays the information that is received from the concerned party(s) and the confined individual.

15. A method of providing personalized visitation services to a confined individual located at a care facility through the use of a professional visitor, comprising the steps of:
   establishing a business relationship between one or more concerned party(s) and the professional visitor for the purposes of communicating with and monitoring the care of the confined individual;

providing a portable computer having a camera and projection system for use by the professional visitor in communicating with the confined individual;

providing a personal computer for use by the concerned party(s) in the transmission of messages to the confined individual by connecting the personal computer with the portable computer through a secure communications network;

conducting a visitation between the concerned party(s) and the confined individual by the professional visitor;

creating a recording of the visitation between the professional visitor and the confined individual;

storing the recording of the visitation on a secured server for the concerned party(s) or the confined individual to access through the secure communications network; and providing a unique security code for the concerned party(s) and the confined individual to access the recording.

16. A method of providing personalized visitation services to a confined individual through the use of an independent third party professional visitation provider, comprising the steps of:

establishing a business relationship between the confined individual and the professional visitation provider;

assigning a visitation specialist to conduct a visitation to the confined individual;

providing an interaction unit for communication between the concerned party(s) and the confined individual;

conducting the visitation between the concerned party(s) and the confined individual by the visitation specialist;

creating a recording of the visitation between the visitation specialist and the confined individual;

storing the recording of the-visitation on a secured server for the concerned party(s) and the confined individual to access through an Internet connection; and providing a unique security code for the concerned party (s) and the confined individual to access the recording of-the visitation on the secured server.

17. A method of providing personalized visitation services to a confined individual located at a care facility through the use of a professional visitor, comprising the steps of:

establishing a business relationship between the confined individual and the professional visitor for the purposes of communicating with and monitoring the care of the confined individual;

providing a portable computer having a camera and projection system for use by the professional visitor in communicating with the confined individual;

providing a personal computer for use by the concerned party(s) in the transmission of messages to the confined individual by connecting the personal computer with the portable computer through a secure communications network;

conducting a visitation between the concerned party(s) and the confined individual by the professional visitor;

creating a recording-of the visitation between the professional visitor and the confined individual;

storing the recording of the visitation on a secured sewer for the concerned party(s) or the confined individual to access through the secure communications network; and providing a unique security code for the concerned party (s) and the confined individual to access the recording.

* * * * *